United States Patent [19]

Cortese et al.

[11] 4,449,983

[45] May 22, 1984

[54] SIMULTANEOUS DELIVERY OF TWO DRUGS FROM UNIT DELIVERY DEVICE

[75] Inventors: Richard Cortese, San Jose; Brian Barclay, Menlo Park; Felix Theeuwes, Los Altos, all of Calif.

[73] Assignee: ALZA Corporation, Palo Alto, Calif.

[21] Appl. No.: 360,589

[22] Filed: Mar. 22, 1982

[51] Int. Cl.³ .............................................. A61M 31/00
[52] U.S. Cl. ................................................... 604/892
[58] Field of Search .............................. 604/890–900; 424/18–25

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,111,202 | 9/1978 | Theeuwes | 128/260 |
| 4,210,139 | 7/1980 | Higuchi | 128/260 |
| 4,298,003 | 11/1981 | Theeuwes et al. | 128/260 |
| 4,350,271 | 9/1982 | Eckenhoff | 604/892 |

Primary Examiner—Benjamin R. Padgett
Assistant Examiner—T. J. Wallen

Attorney, Agent, or Firm—Paul L. Sabatine; Edward L. Mandell; Steven F. Stone

[57] ABSTRACT

An osmotic device is disclosed for delivering two beneficial drugs to an environment of use. The device comprises a wall surrounding a lumen divided into a first compartment containing a drug that is separated by a hydrogel partition from a second compartment containing a different drug. An orifice through the wall communicates with the first compartment for delivering drug formulation from the first compartment, and another orifice through the wall communicates with the second compartment for delivering drug formulation from the second compartment. In operation, drug formulation is dispensed separately from each compartment by fluid being imbibed through the wall into each compartment at a rate controlled by the permeability of the wall and the osmotic pressure gradient across the wall against the drug formulation in each compartment thereby producing in each compartment a solution containing drugs, and by the expansion and swelling of the hydrogel, whereby drug formulation is dispensed through their orifices at a controlled and continuous rate over a prolonged period of time.

18 Claims, 8 Drawing Figures

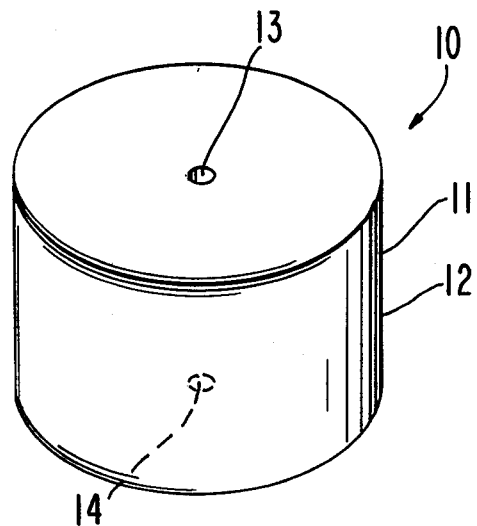
FIG. 1
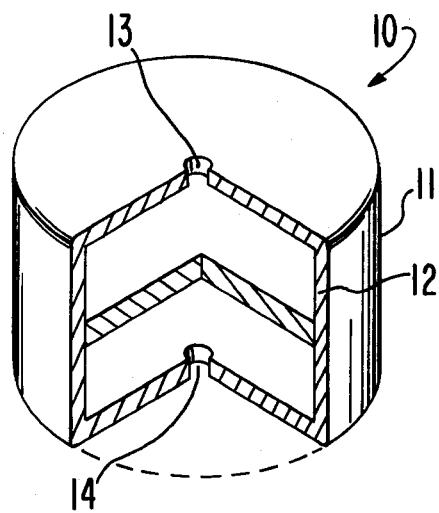
FIG. 2
FIG. 3
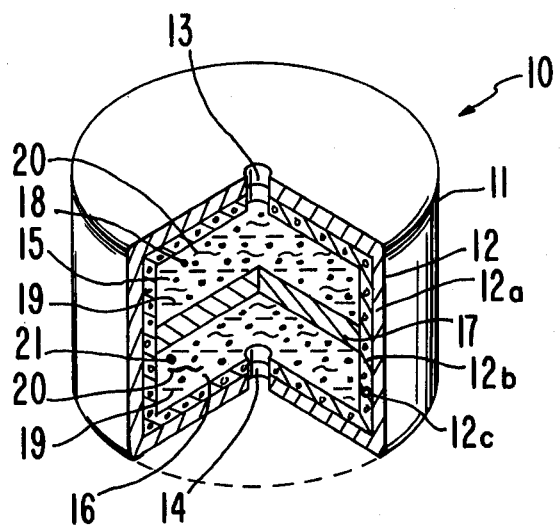

SIMULTANEOUS DELIVERY OF TWO DRUGS FROM UNIT DELIVERY DEVICE

FIELD OF THE INVENTION

This invention pertains to an osmotic system manufactured in the form of an osmotic device. More particularly, the invention relates to an osmotic device that simultaneously delivers two drugs that are separately housed and separately dispensed through separate orifices for (a) obtaining the therapeutic benefits of each drug, (b) lessening the incidence of adverse effects due to the incompatibility of different drugs, or (c) delivering two drugs that are difficult to deliver from a dispensing device.

BACKGROUND OF THE INVENTION

It is frequently desirable to prescribe pharmaceutical dosage forms containing at least two different drugs for obtaining the pharmacological benefits of each drug. The coadministration of certain drugs is prescribed often in fixed ratios for several reasons. For example, for drugs that have the same therapeutic effect but act mechanistically different on the body, such combinations may have the added therapeutic effect of both agents but less side effects, or the drugs may act synergistically and create a larger than additive effect. Also, drug combinations are prescribed for treatments where each individual drug address different symptoms of a particular medical situation. Although, a large number of therapeutic combinations could be provided, often they can not be compounded in the same dosage form because each drug needs to be administered on a different schedule. The different schedule is needed because each drug has a different biological half life and therapeutic index and therefore each drug should be administered in separate dosage forms on a prescribed schedule that is specific for each drug. Thus, a drug that needs to be administered four times a day, should not be combined with a drug that should be administered once a day. These drugs are kinetically incompatible in a pharmaceutical dosage form. Another reason why certain drugs cannot be combined is they may be chemically incompatible or unstable in the presence of each other. This kinetic or chemical incompatibility can be eliminated by the novel dosage form provided by this invention. For example, by using the dosage form provided by this invention, a regimen consisting of four times a day administration of drug can be transformed into a once a day administration such that the drug previously administered four times daily can be combined with a drug administered once daily. In other words, both drugs can be coadministered to the body at delivery rates that are matched to achieve each of their separate therapeutic plasma concentrations. Thus, in the light of the above presentation, it will be appreciated by those versed in the dispensing art, that if a delivery device is made available for housing two or more different drugs at controlled and continuous rates in therapeutically effective amounts for obtaining the benefits of each drug, such a delivery device would have a definite use and be a valuable contribution to the dispensing art.

OBJECTS OF THE INVENTION

Accordingly, it is an immediate object of this invention to provide an osmotic device that contributes to the dispensing art by making available a device that can dispense at least two different drugs at controlled rates for obtaining the pharmacological and physiological benefit of each drug, and which device thusly represents an improvement and an advancement in the delivery arts.

Another object of the invention is to provide an osmotic device for separately housing and separately dispensing at least two drugs, and which device overcomes the problems known to the prior art.

Another object of the invention is to provide an osmotic device that can separately dispense at independently controlled rates and independently continuously deliver two or more drugs to biological drug receptors over a prolonged period of time.

Still another object of the invention is to provide an osmotic device having two compartments each containing a drug that can be from insoluble to very soluble in an aqueous fluid, and an expandable partition between the compartment, which expandable partition operates to diminish the volume occupied by the drug in each compartment, thereby delivering each agent from the device at a controlled rate over time.

Still a further object of the invention is to provide an osmotic device that can administer independently two different drugs from two compartments separated by a layer of an expandable driving member formed of a hydrogel, and which device provides a complete pharmaceutical regimen for the two drugs to a warm-blooded animal for a particular time period, the use of which requires intervention only for initiation and possibly termination of the regimen.

Yet still another object of the invention is to provide an osmotic device for dispensing separately two different drugs in known amounts per unit time, and which device can continuously maintain substantially the major amount of the drugs present in the device as a saturated solution throughout their period of release from the device.

Yet still another object of the invention is to provide an osmotic device that can deliver separately two different drugs by using an expandable driving member that continuously increases its volume while correspondingly decreasing the volume occupied by each drug for maintaining excess drug in the device over an increased length of time.

Other objects, features and advantages of the invention will be more apparent to those versed in the art from the following specification, taken in conjunction with the drawings and the accompanying claims.

BRIEF DESCRIPTION OF THE DRAWINGS

In the drawings figures, which are not drawn to scale, but are set forth to illustrate various embodiments of the invention, the drawing figures are as follows:

FIG. 1 is a view of an osmotic device designed and adapted for orally administering two beneficial drugs;

FIG. 2 is an opened view of the osmotic device of FIG. 1 illustrating the structure of the device comprising a semipermeable wall;

FIG. 3 is an opened view of the osmotic device of FIG. 1 illustrating the device comprising a laminated wall;

In the drawings and specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 4:
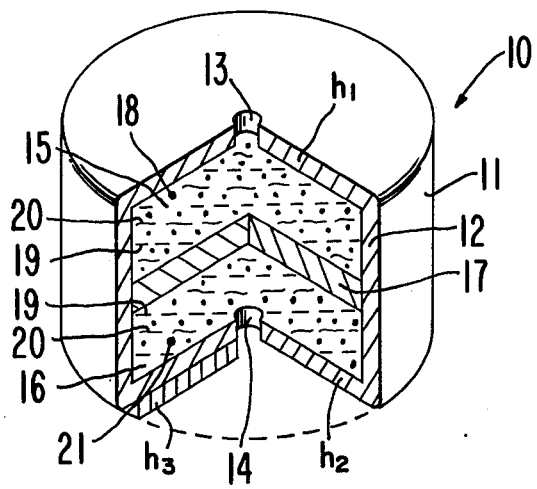
FIG. 4 is an opened view of the osmotic device of FIG. 1 illustrating the structure and the operation of the device made with an added lamina.

Turning now to the drawings in detail, which are an example of various osmotic delivery devices provided by the invention, and which example is not to be considered as limiting, one example is the osmotic device illustrated in FIGS. 1 through 4 and designated by the numeral 10. In FIG. 1, osmotic device 10 comprises a body 11 having a wall 12 with a first orifice 13 in wall 12 and a second orifice 14 in wall 12 for communicating the exterior of device 10 with the internal lumen of device 10.

Wall 12 of osmotic device 10, as seen in opened section in FIG. 2, comprises a semipermeable material that is permeable to the passage of an external fluid and it is essentially impermeable to the passage of drug and osmagent. Wall 12 is substantially inert, it maintains its physical and chemical integrity during the dispensing of the beneficial drugs, and it is non-toxic to animals including humans. Wall 12 of osmotic device 10, as seen in an embodiment in opened-section in FIG. 3, comprises a laminate formed of semipermeable lamina 12a in laminar arrangement with a microporous lamina 12b. Microporous lamina 12b consists of micropores 12c that are preformed micropores, or the micropores are formed in the environment of use. Microporous lamina 12b is formed of materials that are inert and non-toxic. In FIG. 3, device 10 is manufactured in the embodiment illustrated with microporous lamina 12b facing the inside of device 10, and with the semipermeable lamina 12a facing the exterior of device 10. In another embodiment, device 10 can be manufactured with microporous lamina 12b positioned outside facing the environment of use and with semipermeable lamina 12a positioned inside of device 10. Both the semipermeable lamina and the microporous lamina can contain additional wall forming agents such as flux enhancers, flux reducers, plasticizers, and the like.

In FIG. 3, device 10 is seen in opened-section for illustrating the structure of device 10. While the internal structure of FIG. 3 is described in detail, it is understood the detailed description can be applied to FIG. 2. In FIG. 3, wall 12 surrounds and forms an internal lumen divided into a first compartment 15 and a second compartment 16. Compartment 15 and compartment 16 are separated by a partition 17 formed of an expandable, swellable hydrogel material. First orifice 13 communicates with first compartment 15 and second orifice 14 communicates with the second compartment 16. Compartment 15, in one embodiment, contains a beneficial drug 18, represented by dots, that is soluble to very soluble in an external fluid and it exhibits an osmotic pressure gradient across wall 12 against the fluid 19, indicated by dashes, that is imbibed into first compartment 15. First compartment 15, in another embodiment contains drug 18 that has limited solubility or it is substantially insoluble in fluid 19 imbibed into compartment 15, and it exhibits a limited, or it may not exhibit any osmotic pressure gradient across wall 12 against the exterior fluid. In this latter embodiment, drug 18 optionally is mixed with an osmagent 20, indicated by wavy lines, that is soluble in the external fluid and it exhibits an osmotic pressure gradient across wall 12 against the fluid. Second compartment 16 contains a different drug 21 than the drug in the first compartment. Drug 21 is soluble to very soluble in the external fluid and it exhibits an osmotic pressure gradient across wall 12 against the fluid that is imbibed into second compartment 16. In another embodiment, drug 21 has limited solubility, or it is substantially insoluble in the fluid imbibed in compartment 16, and it exhibits a limited, or it may not exhibit any osmotic pressure gradient across wall 12 against the exterior fluid. In this embodiment, drug 21 optionally is mixed with an osmagent 20 that is soluble in the external fluid and exhibits an osmotic pressure gradient across wall 12 for aiding in dispensing drug 21 from the device. The osmagent can be the same or different in the first compartment and the second compartment.

Partition 17 in device 10 is made of a hydrogel material. Hydrogel partition 17 possesses osmotic properties. Partition hydrogel 17 absorbs fluid imbibed into device 10 and swells or expands to some equilibrium state. At equilibrium the osmotic pressure of the hydrogel approximately equals the swelling pressure of the hydrogel, and the osmotic pressure of the hydrogel network is the driving force of the swelling, expanding partition 17 as it moves into compartment 15 and compartment 16 to urge drug formulation through orifice 13 and orifice 14 for delivering from device 10. That is, device 10 releases drugs through orifices 13 and 14 by fluid being imbibed into device 10 in a tendency towards osmotic equilibrium at a rate determined by the permeability of wall 12 and the osmotic pressure gradient across wall 12. The imbibed fluid continuously forms a solution containing drug in each compartment, or a solution of osmagent containing drug in suspension in the compartments, which solution in either instance in both compartments is released by the combined operations of device 10. These operations include the solution being osmotically delivered through orifices 13 and 14 due to the continuous formation of solution in the compartments, and by the hydrogel swelling, increasing in volume, and applying pressure against the solutions in the compartments, thereby delivering the drugs to the exterior of device 10.

Partition hydrogel 17 operates to substantially insure that drug is delivered from each compartment at a constant rate over a prolonged period of time by two methods. First, the hydrogel operates to continuously concentrate drug in each compartment by imbibing some fluid from each compartment to keep the concentration of the drugs from falling below saturation. Secondly, the hydrogel by imbibing external fluid across the wall continuously increases its volume, thereby exerting a force on drug 18 and drug 21 and diminish the volume of compartments 15 and 16, thusly concentrating drug 18 and drug 21 in compartments 15 and 16. The swelling and expansion of the hydrogel, with its accompanying increase in volume, along with the simultaneous, corresponding reduction in volume of the compartments, assures the delivery of drug 18 and drug 21 at a controlled rate over time.

The osmotic delivery system as seen in FIGS. 1 through 3 can be made into many embodiments including the presently preferred embodiments for oral use, that is, for releasing locally or systemically acting therapeutic medicaments in the gastrointestinal tract over a prolonged period of time. The oral system can have various conventional shapes and sizes such as round with a diameter of ⅛ inch to ½ inch, or it can be shaped like a capsule having a range of sizes from triple zero to zero, and from 1 to 8. In these manufactures system 10 can be adapted for administering drug to numerous animals, including warm blooded mammals, avians, reptiles and pisces.

While FIGS. 1 through 3 are illustrative of various delivery systems that can be made according to the invention, it is to be understood these systems are not to be considered as limiting, as the system can take a wide variety of shapes, sizes and designs adapted for delivering the drug to different biological environments of use. For example, the delivery system includes anal-rectal, artificial gland, blood system, buccal, cervical, dermal, ear, implant, intrauterine, nasal, subcutaneous, vaginal, and the like.

DETAILED DESCRIPTION OF THE INVENTION

In accordance with the practice of this invention it has now been found an osmotic delivery system can be made for delivering at least two different drugs independently and simultaneously to a biological environment of use. The delivery system comprises the two compartments as seen in FIGS. 1 to 3 discussed above, with the drugs delivered independently from each compartment. The system described here is made with the same membrane composition and thickness on each compartment. The delivery equation for each osmotic compartment is given by equation 1.

$$\frac{dm}{dt} = \frac{K A \Delta \pi S_D}{h} \quad (1)$$

wherein K is the water permeability constant for the wall, A is the area of exposed surface of a compartment, $\Delta\pi$ is the difference between the osmotic pressure in a compartment compared with the external osmotic pressure, $S_D$ is the solubility of the drug in fluid that enters the compartment, and h is the thickness of the wall of the device. The ratio of release rates from compartment 1, the first compartment, to compartment 2, the second compartment, is given by equation 2.

$$\frac{\frac{dm}{dt}1}{\frac{dm}{dt}2} = \frac{\frac{K_1 A_1 \Delta\pi_1 S_{D1}}{h_1}}{\frac{K_2 A_2 \Delta\pi_2 S_{D2}}{h_2}} = \frac{A_1 \Delta\pi_1 S_{D1}}{A_2 \Delta\pi_2 S_{D2}} \quad (2)$$

wherein the K, A, $\pi$, and $S_D$ are as defined, and the wall on compartment 1 and compartment 2 are similar for homogenous walls, that is, the wall permeability $K_1 = K_2$, and the wall thickness $h_1 = h_2$, wherein $h_1$ is the wall thickness of compartment 1, and $h_2$ is the wall thickness of compartment 2. Equation 2 reveals that the ratio of delivery of one drug from one compartment to another drug from the other compartment is dependent only on the properties of the drugs, their associated osmagents, and surface areas of the compartments. The relative release rate from each compartment is modified or changed, by changing the composition in each compartment, and not the composition of the wall. Alternatively, the two compartments can be manufactured to have separate wall compositions and/or thicknesses such that the two rates can be engineered independently of each other using also the membrane properties. Such a structure can be achieved by coating the total system with the same membrane and subsequently layering a separate laminate with thickness $h_3$ onto either compartment (1) or (2), as illustrated in FIG. 4, wherein $h_1$ is the thickness of the wall surrounding the first compartment, $h_2$ is the thickness of the wall at the second compartment, and $h_3$ is the thickness of the lamina added to the second compartment. Lamina $h_2$ can be formed of a different semipermeable material, a material impermeable to fluid, a material that bioerodes over time, and the like.

The materials forming the semipermeable wall of the delivery device are those that do not adversely affect the drug and the osmagent, an animal body, or other host, is permeable to an external fluid, such as water and biological fluid, while remaining essentially impermeable to drug, osmagents, and the like. The selectively permeable materials forming wall 12 are insoluble in body fluids, they are non-erodible, or they can be made to bioerode after a predetermined period with bioerosion corresponding to the end of the drug release period. Typical materials for forming wall 12 include semipermeable materials known to the art as osmosis and reverse osmosis polymers. The semipermeable polymers include cellulose acylate, cellulose diacylate, cellulose triacylate, cellulose acetate, cellulose diacetate, cellulose triacetate, beta-glucan acetate, acetaldehyde dimethyl acetate, cellulose acetate ethyl carbamate, polyamide, polyurethane, sulfonated polystyrene, cellulose acetate phthalate, cellulose acetate methyl carbamate, cellulose acetate succinate, cellulose acetate dimethylaminoacetate, cellulose acetate chloroacetate, cellulose dipalmitate, cellulose dioctanoate, cellulose dicaprylate, cellulose dipentanlate, cellulose acetate valerate, cellulose acetate p-toluenesulfonate, cellulose acetate butyrate, selectively permeable polymers formed by the coprecipitation of a polycation and a polyanion as disclosed in U.S. Pat. Nos. 3,173,876; 3,276,586; 3,541,005; 3,541,006 and 3,546,142. Generally, semipermeable materials useful for forming wall 12 will have a fluid permeability of $10^{-5}$ to $10^{-1}$ (cc·mil/cm$^2$·hr·atm) expressed per atmosphere of hydrostatic or osmotic pressure across wall 12 at the temperature of use. Other suitable materials are known to the art in U.S. Pat. Nos. 3,845,770; 3,916,899; 4,036,228 and 4,111,202.

The microporous materials comprising microporous lamina 12b maintains their physical and chemical integrity during the period of time drug is released from system 10. The microporous materials comprising lamina 12b generally can be described as having a sponge-like appearance that provides a supporting structure for microscopic sized interconnected pores or voids. The materials can be isotropic wherein the structure is homogenous throughout a cross-sectional area, or the materials can be anisotropic wherein the structure is non-homogenous throughout a cross-sectional area, or the materials can have both cross-sectional areas. The materials are opened-celled, as the micropores are continuous or connected, with pores having an opening on both faces of the microporous lamina. The micropores are interconnected through tortuous paths of regular and irregular shapes including linear, curved, curved-linear, randomly oriented continuous pores, hindered connected pores, and other interconnected porous paths discernable by microporous examination.

Generally, the microporous lamina are characterized as having a reduced bulk density as compared to the bulk density of the corresponding non-porous microporous lamina. The morphological structure of the total microporous wall have a greater proportion of total surface area than the non-porous wall. The microporous wall can be further characterized by the pores size, the number of pores, the tortuosity of the microporous paths, and the porosity which relates to the size and the number of pores. Generally, material possessing from 5% to 95% pores, and having a pore size of from 10 angstroms to 100 microns can be used for making the microporous lamina.

Materials useful for making the microporous lamina include polycarbonates comprised of linear polyesters of carbonic acid in which carbonate groups recur in the polymer chain, microporous materials prepared by the phosgenation of a dihydroxyl aromatic such as bisphenol, a microporous poly(vinylchloride), microporous polyamides such as polyhexamethylene adipamide, microporous modacrylic copolymers including those formed from poly(vinylchloride) and acrylonitrile, microporous styrene-acrylic and its copolymers, porous polysulfones characterized by diphenylene sulfone in a linear chain thereof, halogenated poly(vinylidene), polychloroethers, acetal polymers, polyesters prepared by esterification of a dicarboxylic acid or anhydride with an alkylene polyol, poly(alkylenesulfides), phenolics, polyesters, microporous polysaccharides having substituted anhydroglucose units exhibiting a decrease permeability to the passage of water and biological fluids, asymmetric porous polymers, cross-linked olefin polymers, hydrophobic or hydrophilic microporous homopolymers, copolymers or interpolymers having a reduced bulk density, and materials described in U.S. Pat. Nos. 3,595,752; 3,643,178; 3,654,066; 3,709,774; 3,718,532; 3,803,601; 3,852,224; 3,852,388; and 3,853,601; in British Pat. No. 1,126,849; and in Chem. Abst. Vol. 71, 427F, 22573F, 1969.

Additional microporous materials for forming microporous lamina 12b include poly(urethane), cross-linked chain-extended poly(urethane), poly(imides), poly(benzimidazoles), collodion, regenerated proteins, semisolid cross-linked poly(vinyl-pyrrolidone), microporous materials prepared by diffusion of multivalent cations into polyelectrolyte sols, microporous derivatives of poly(styrene) such as poly(sodium-styrene-sulfonate), poly(vinyl benzyl trimethyl-ammonium chloride), microporous cellulosic acylates and the like microporous polymers are known in U.S. Pat. Nos. 3,524,753; 3,565,259; 3,276,589; 3,541,055; 3,541,006; 3,546,142; 3,615,024; 3,646,178; and 3,852,224.

The pore-formers useful for forming the microporous lamina in the environment of use include solids and pore-forming liquids. The term pore-former as used herein also embraces micropath formers, and removal of the pore and/or pore-former leads to both embodiments. In the expression pore-forming liquids, the term for this invention generically embraces semi-solids and viscous fluids. The pore-formers can be inorganic or organic and the lamina forming polymer usually contains from 5 to 70% by weight of the pore-former, and more preferably about 20 to 50% by weight. The term pore-former for both solids and liquids include substances that can be dissolved, extracted or leached from the precursor microporous wall by fluid present in the environment of use to form capable, open-celled type microporous lamina. The pore-forming solids have a size of about 0.1 to 200 microns and they include alkali metal salts such as lithium carbonate, sodium chloride, sodium bromide, potassium chloride, potassium sulfate, potassium phosphate, sodium acetate, sodium citrate, and the like. Organic compounds such as polysaccharides including the sugars sucrose, glucose, fructose, mannitol, mannose, galactose, sorbitol and the like. They can be polymers soluble in the environment of use such as Carbowaxes ®, Carbopol ®, and the like. The pore-formers embrace diols, polyols, polyhydric alcohols, polyalkylene glycols, polyglycols, poly($\alpha$-$\omega$)-alkylenediols, and the like. The pore-formers are non-toxic and on their removal from lamina 12b, channels and pores are formed through the lamina that fill with fluid present in the environment of use.

The partition between the first and second compartment is formed of a hydrogel, that is, a swellable, hydrophilic polymer. The hydrogels exhibit the ability to swell in the presence of water and retain a significant fraction of water within its structure. In one embodiment, the hydrogel polymers are lightly cross-linked, such cross-links being formed by covalent or ionic bonds, which hydrogels interact with imbibed water and aqueous biological fluids and swell or expand to some equilibrium state. The hydrogels can be of plant or animal origin, hydrogels prepared by modifying naturally occurring structures, or synthetic polymeric hydrogels. The polymers swell or expand to a very high degree, usually exhibiting a 2 to 50 fold volume increase. Hydrophilic polymeric materials useful for the present purpose include poly(hydroxyalkyl methacrylate), poly(N-vinyl-2-pyrrolidone), anionic and cationic hydrogels, hydrogel polyelectrolyte complexes, poly(vinyl alcohol) having a low acetate residual and lightly cross-linked with a member selected from the group consisting essentially of glyoxal, formaldehyde, and glutaraldehyde, a mixture of cross-linked agar and carboxymethyl cellulose, methyl cellulose cross-linked with a dialdehyde, a water insoluble, water-swellable copolymer produced by forming a dispersion of finely divided copolymer of maleic anhydride with styrene, ethylene, propylene, butylene or isobutylene cross-linked with from 0.001 to about 0.5 moles of a polyunsaturated cross-linking agent per mole of maleic anhydride in the copolymer, water-swellable polymers of N-vinyl lactams, and the like. Generally, the partition will have a thickness of about 2 to 30 mils and will function to maintain the integrity of the first and second compartments.

Additional hydrogel-forming agents that can be used for making the expandable partition include polysaccharides, polysaccharides with basic, carboxyl or other acid groups such as natural gum, seaweed extract, plant exudate, seed gum, plant extract, animal extract, or a biosynthetic gum. Typical gel-forming agents include agar, agarose, algin, sodium alginate, potassium alginate, carrageenan, kappa-carrageenan, lambda-carrageenan, fucoidan, furcellaran, laminaran, hypnea, eucheuma, gum arabic, gum ghatti, gum karaya, gum tragacanth, guar gum, locust bean gum, quince psyllium, flax seed, okra gum, arabinoglactin, pectin, xanthan, scleroglucan, dextran, amylose, amylopectin, dextrin, and the like.

Other hydrogel polymers presently preferred for forming the partition include poly(ethylene oxide) having a molecular weight of 100,000 to 5,000,000 and commercially available as Polyox ® polymer, hydrophilic hydrogels comprising a carboxypolymethylene, a carboxyvinyl polymer available as Carbopol ® polymer, Cyanamer ® polyacrylamides, cross-linked water-swellable indene-maleic anhydride polymers, Goodrite ® polyacrylic acid, starch graft copolymers, Aquakeeps acrylate polymer, diester cross-linked polyglucan, and the like. The hydrogels are known to the prior art in U.S. Pat. Nos. 3,865,108; 4,002,173; 4,169,066; 4,207,893, 4,211,681; 4,271,143; and 4,277,366, and in *Handbook of Common Polymers,* by Scott and Roff, published by the Chemical Rubber Company, Cleveland, Ohio.

The polymers used for forming lamina $h_3$ additionally include polyethylene, polypropylene, polyacrylonitrile, regenerated protein, erodible polyglycolic acid, polyorthoester, and the like.

The expression orifice as used herein comprises means and methods suitable for releasing the drug from each compartment. The orifice will pass through the semipermeable wall, or through the semipermeable-microporous laminated wall for communicating each compartment with the exterior of the device. The expression includes passageway, or bore through wall formed by mechanical procedures or by eroding an erodible element, such as a gelatin plug in the environment of use. Generally, for the purpose of the invention the orifices will have a cross-sectional area of 2 to 15 mils. A detailed description of osmotic orifices and the maximum and minimum dimensions for an orifice are disclosed in the U.S. Pat. Nos. 3,845,770 and 3,916,899.

The osmagents, or osmotically effective compounds that can be used in the first compartment or in the second compartment include organic and inorganic compounds or solutes that exhibit an osmotic pressure gradient across the semipermeable wall, or the laminated wall against an external fluid. Osmagents, or osmotically effective compounds include magnesium sulfate, magnesium chloride, sodium chloride, lithium chloride, potassium sulfate, potassium acid phosphate, mannitol, urea, sucrose, and the like. Osmagents are known to the art in U.S. Pat. Nos. 3,854,770; 4,077,407; and 4,235,236.

The term drug as used in the specification and the accompanying claims includes physiologically or pharmacologically active substances that produce a localized or systemic effect or effects in animals, avians, pices and reptiles. The active drug that can be delivered includes inorganic and organic compounds without limitation, those materials that act on the central nervous system such as hypnotics, sedatives, psychic energizers, tranquilizers, anticonvulsants, muscle relaxants, antiparkinson agents, analgesics, anti-inflammatory, local anesthetics, muscle contractants, anti-microbials, anti-malarials, hormonal agents, contraceptives, sympathomimetics, diuretics, anti-parasites, neoplastics, hypoglycemics, nutritional agents, ophthalmic, electrolytes, and the like. The drug housed and delivered from each compartment in a presently preferred embodiment embraces a different drug in the first compartment and in the second compartment respectfully, as represented by the following: anti-inflammatory and anti-pyretic, anti-inflammatory and analgesic, bronchodilator and vasodilator, beta-blocker and diuretic, beta-blocker and vasodilator, beta-agonist and muscle relaxant, beta-adrenergic agonist and histamine receptor antagonist, and decongestant, beta-adrenergic stimulator and muscle relaxant, anti-hypertensive and diuretic, analgesic and analgesic antispasmotic and anticholenergic, tranquilizer and anticholenergic, anticholenergic and histamine receptor antagonist, and the like. The phrase drug formulation indicates drug, or drug mixed with an osmagent present in, or released from the device to the environment of use.

Exemplary drugs that are very soluble in water and can be delivered by the devices of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridihexethyl chloride, phenformin hydrochloride, methylphenidate hydrochloride, oxprenolol hydrochloride, metoprolol tartrate, cimetidine hydrochloride, and the like.

Exemplary drugs that are poorly soluble in water and that can be delivered by the devices of this invention include diphenidol, meclizine hydrochloride, prochlorperazine maleate, phenoxybenzamine, thiethylperazine maleate, anisindone, diphenadione erythrityl tetranitrate, dizoxin, isofurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, esterogenic progestational, corticosteriods, hydrocortisone, hydrocorticosterone acetate, cortisone acetate, triamcinolone, methyltesterone, 17$\beta$-estradiol, ethinyl estradiol, ethinyl estradiol 3-methyl ether, prednisolone, 17$\beta$-hydroxyprogesterone acetate, 19-nor-progesterone, norgestrel, norethindone, norethiderone, progesterone, norgesterone, norethynodrel, and the like. The amount of drug in each compartment generally is from 0.05 ng to 800 mg, with individual compartments containing 1 mg. 5 mg, 100 mg, 250 mg, 500 mg, and the like. The beneficial drugs are known to the art in *Pharmaceutical Sciences,* by Remington, 14th Ed., 1970 published by Mack Publishing Co., Easton, PA; in *American Drug Index,* 1976, published by J. B. Lippincott Co., Philadelphia, PA, in *The Drug, The Nurse, The Patient, Including Current Drug Handbook,* 1974–1976, by Falconer et al. published by Saunder Company, Philadelphia PA; and in *Medicinal Chemistry,* 3rd Ed., Vol. 1 and 2, by Burger, published by Wiley-Interscience, New York.

The drug can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate, and salicylate. For acid drugs, salts of metals, amines or organic cations, for example quaternary ammonium can be used. Derivatives of drugs such as esters, ethers and amides can be used. Also, a drug that is water insoluble can be used in a form that is a water soluble derivative thereof to serve as a solute, and on its release from the device, is converted by enzymes, hydrolyzed by body pH or other metabolic processes to the original biologically active form. The drug can be present in the compartment with a binder, dispersant, wetting agent, suspending agent, lubricant and dye. Representative of these include suspending agents such as colloidal magnesium silicant, collidal silicon dioxide, and calcium silicate; binders like polyvinyl pyrrolidone, and magnesium stearate, wetting agents such as fatty amines, fatty quaternary ammonium salts, and the like. The drug can also be present in the compartments mixed with a dye for aiding in identifying the drug in each compartment.

The solubility of a drug in the fluid that enters the compartments can be determined by known techniques. One method consists of preparing a saturated solution comprising the fluid plus the drug as ascertained by analyzing the amount of drug present in a definite quantity of the fluid. A simple apparatus for this purpose consists of a test tube of medium size fastened upright in a water bath maintained at constant temperature and pressure, in which the fluid and the drug are placed and stirred by a rotating glass spiral. After a given period of stirring, a weight of the fluid is analyzed and the stirring continued an an additional period of time. If the analysis shows no increase of dissolved drug after successive periods of stirring, in the presence of excess solid drug in the fluid, the solution is saturated and the results are taken as the solubility of the drug in the fluid. If the drug is soluble, an added osmotically effective compound optionally may not be needed, if the drug has limited solubility in the fluid, then an osmotically effective compound can be incorporated into the device. Numerous other methods are available for the determination of the solubility of a drug in a fluid. Typical methods used for the measurement of solubility are chemical and electrical conductivity. Details of various methods for determining solubilities are described in *United States Public Health Service Bulletin*, No. 67 of the Hygenic Laboratory; *Encyclopedia of Science and Technology*, Vol. 12, pages 542 to 556, 1971, published by McGraw-Hill, Inc,; and *Encyclopedia Dictionary of Physics*, Vol. 6, pages 547 to 557, 1962, published in Pergamon Press, Inc. For the purpose of the invention, the phrase drugs with degrees of solubility as used herein indicates, drugs that are insoluble to very soluble in aqueous and biological fluids. Further for this purpose, an insoluble drug indicates a solubility of less than 25 mg of drug in a ml of fluid, a poorly soluble drug is one that dissolves in the range of about 25 mg to 150 mg of drug per ml of fluid, a soluble drug dissolves about 150 mg to 600 mg of drug per ml of fluid, and a very soluble drug dissolves in excess of 600 mg of drug per ml of fluid. While the presently preferred embodiments have been described with reference to poorly or very soluble drugs it is to be understood the device can be used to deliver other drugs.

Polymeric hydrogel imbibition pressure determinations can be used for selecting a hydrogel useful for the present purpose. A determination can be made by using the following procedure. A $\frac{1}{2}$ inch round die, fitted with a $\frac{1}{2}$ inch diameter stainless steel plugs, is charged with a known quantity of polymer with the plugs extending out either end. The plugs and the die were placed in a Carver press with plates between 200° and 300° F. A pressure of 10,000 to 15,000 PSI was applied to the plugs. After 10 to 20 minutes of heat and pressure the electrical heating to the plates were turned off, and tap water circulated through the plates. The resulting $\frac{1}{2}$ inch discs were placed in an air suspension coater charged with 1.8 kg saccharide cores and coated with cellulose acetate having an acetyl content of 39.8% dissolved in 94:6 w/w, $CH_2Cl_2/CH_3OH$, to yield a 3% w/w solution. The coated systems were dried overnight at 50° C. The coated discs were immersed in water at 37° C. and periodically removed for a gravimetric determination of water imbibed. The initial imbibition pressure was calculated by using the water transmission constant for the cellulose acetate, after normalizing imbibition values for membrane surface area and thickness. The polymer used in this determination was the sodium derivative of Carbopol-934® polymer, prepared according to the procedure of B. F. Goodrich Service Bulletin GC-36, "Carbopol® Water-Soluble Resins," page 5, published by B. F. Goodrich, Akron, Ohio.

The cumulative weight gain values, y, as a function of time, t, for the water soluble polymer disc coated with the cellulose acetate were used to determine the equation of the line $y = c + bt + at^2$ passing through those points by a least square fitting technique.

The weight gain for the Na Carbopol-934 is given by equation as follows: Weight Gain equals $0.359 + 0.665t - 0.00106t^2$ wherein t is elapsed time in minutes. The rate of water imbibition at any time will be equal to the slope of the line, that is given by the following equations:

$$\frac{dy}{dt} = \frac{d(0.359 + 0.665t - 0.00106t^2)}{dt}$$

$$\frac{dy}{dt} = 0.665 - 0.00212t$$

To determine the initial rate of water absorption the derivative is evaluated at $t = 0$, that is $dy/dt = 0.665$ $\mu l/min$, which is equal to the coefficient b. Normalizing the imbibition rate for membrane surface area 2.86 cm$^2$ and thickness 0.008 cm, imbibition pressure $\pi$ may be determined from the following equation $$K\pi = 0.665\ \mu l/min \times \left(\frac{60\ min}{hr}\right) \times \left(\frac{1\ ml}{1000\ \mu l}\right) \left(\frac{0.008\ cm}{2.86\ cm^2}\right)$$

and the knowledge of the water permeability constant k of the cellulose acetate used in the experiment. The K value for cellulose acetate used in this experiment calculated from NaCl imbibition values is found to be $1.9 \times 10^{-7}$ cm$^2$/hr atm.

Substituting into the calculated $K\pi$ expression $(1.9 \times 10^{-7}$ cm$^2$/hr.atm$)$ $(\pi) = 1.13 \times 10^{'4}$ cm$^2$/hr, $\pi = 600$ atm at $t = 0$. As a method for evaluating the efficiency of a polymer with respect to duration of zero-order driving force, the % of water uptake was selected before the water flux values decreased to 90% of their initial values. The value of the initial slope for the equation of a straight line emanating from the % weight gained axis will be equal to the initial value of dy/dt evaluated at $t = 0$, with the y intercept c defining the linear swelling time, with $(dy/dt)0 = 0.665$ and the y intercept = 0.359, which yields $y = 0.665t + 0.359$. In order to determine when the value of the cumulative water uptake is 90% of the initial rate, the following expression is solved for t, $$0.9 = \frac{at^2 + bt + c}{bt + c} = \frac{\Delta w}{w} \cdot 9$$

Figure 5:
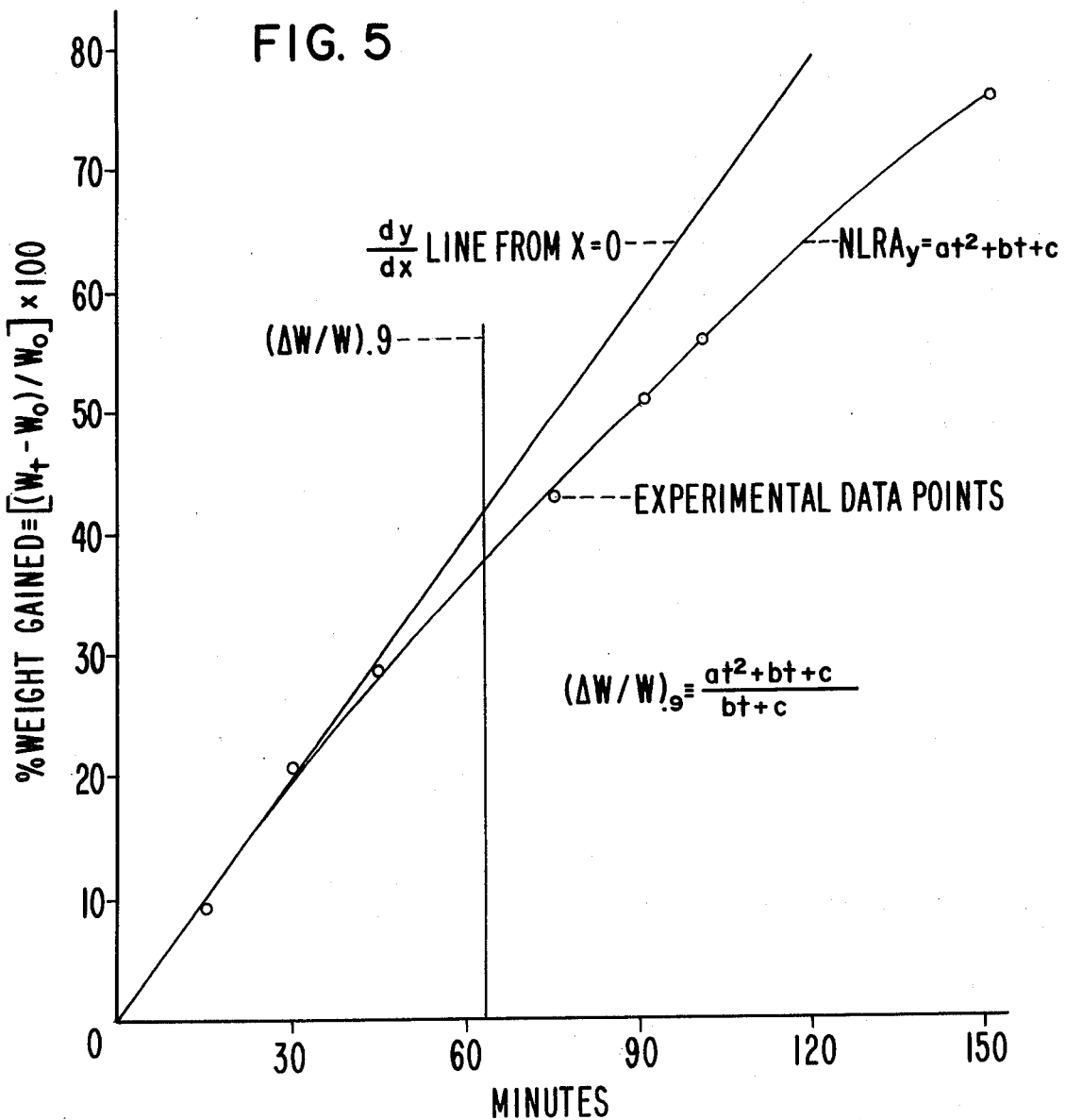
FIG. 5 represents the cumulative weight gain, as a function of time, of a polymer disc enclosed in a semipermeable membrane when the disc is submersed in water.

-continued $$\frac{-0.00106\,t^2 + 0.665\,t + 0.359}{0.665t + 0.359} = 0.9,$$

and solving for t, $$-0.00106t^2 + 0.0665t + 0.0359 = 0$$

$$t = \frac{-0.0665 \pm [(0.0665)^2 - 4(-0.00106)(0.0359)]^{\frac{1}{2}}}{2(-0.00106)}$$

t=62 min and the weight gain is $-0.00106(62)^2+(0.665)(62)+0.359=38$ μl, with the initial sample weight=100 mg, thus (Δw/w). 9×100=38%. An example of such imbibition results are shown in FIG. 5.

Figure 6:
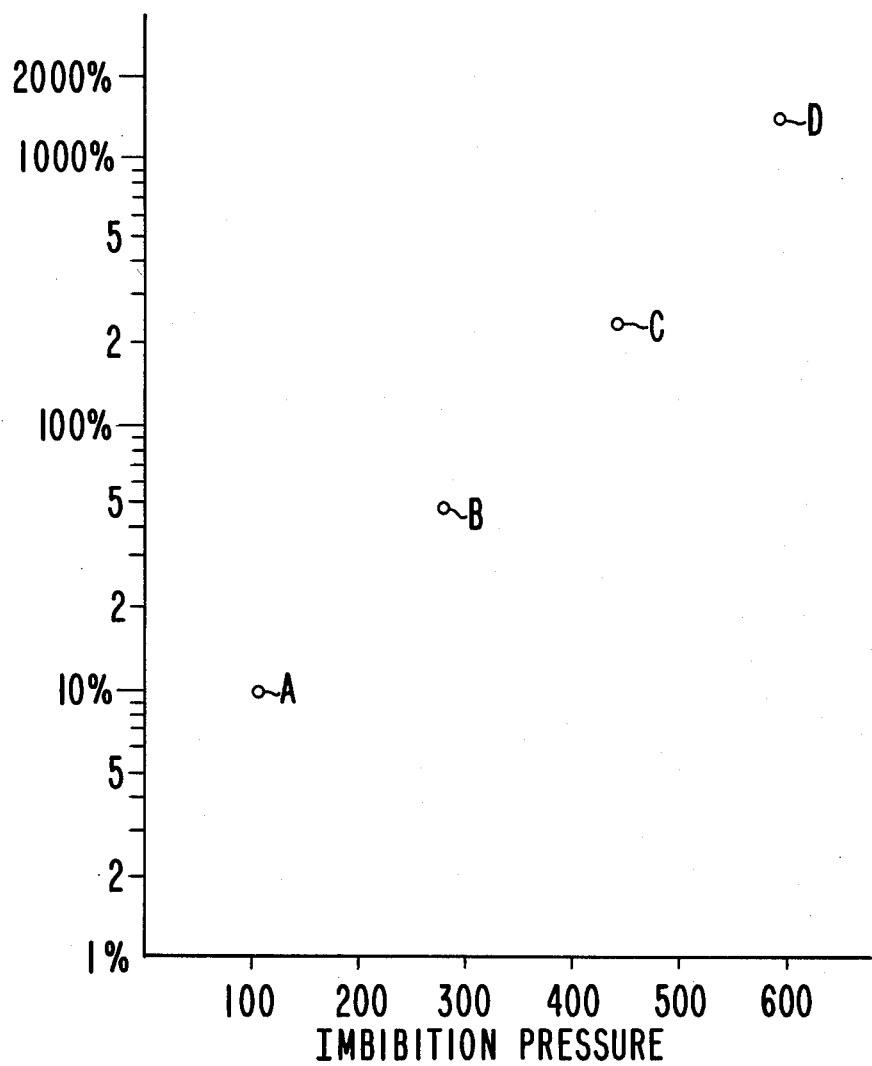
FIG. 6 is a graph depicting the percent weight uptake that polymers A, B, C, and D respectively exhibit in a saturated solution of sodium chloride in water as a function of their osmotic imbibation pressures.

The selection of a hydrogel for forming a partition further can be made by determining the interaction at the hydrogel-water drug interface. This can be ascertained by placing a film formed of a hydrogel in contact with an aqueous solution containing drug, and sometimes an osmagent, and observing the modification of the hydrogel at the hydrogel-aqueous drug environment. Modification of the surface of the polymeric hydrogel, during operation of the device, in situ, leads to an in situ formed precipitate in its outer surface of the hydrogel, thereby indicating the hydrogel and the solution containing drug are suitable for operating as a partition in the device. A representative procedure that can be used consists in measuring the percent weight gain for various polymers immersed in a saturated solution of a drug or an osmagent. The procedure broadly indicates interface absorption activity. That is, if there is little absorption by the polymer, there is correspondingly a little gain in weight and the polymer is suitable for use as a partition. Similarly, if there is a large gain in weight, indicating a large volume absorbed, the polymer is not preferred as a partition for a highly water soluble drug. FIG. 6 represents the percent weight gain for 4 polymers immersed in a saturated solution of NaCl as a function of the imbibition pressure of the polymer. In FIG. 6, the polymers are as follows: A is Klucel H ® polymer; B is Polyox COAG ® polymer; C is Carbopol-934 ® polymer; and D is Na Carbopol-934 ® polymer. The samples were periodically removed from the solution, and the surface solution blotted and the polymer weighed. The equilibrium weight gain is defined as that point where no further increase in weight was measured over time. Other methods that can be used for studying the hydrogel solution interface include rheologic analysis, viscometric analysis, ellipsometry, contact angle measurements, electrokinetic determinations, infrared spectroscopy, optical microscopy, interface morphology and microscopic examination of an operative device.

The osmotic device of the invention is manufactured by standard techniques. For example, in one manufacture, a drug and optionally an osmagent and other ingredients that may be housed in one compartment are mixed into a solid, semi-solid, moist, or pressed state by conventional methods such as ballmilling, calendering, stirring or rollmilling, and then pressed into a preselected shape. A partition is formed by molding, spraying or dipping one surface of the pressed shape into the partition forming material. The second compartment is formed by pressing a drug, or optionally a drug and an osmagent into a preselected shape that corresponds to the above formed shape, and then intimately attaching it to the partition, or a drug and an osmagent can be pressed directly onto the partition. Finally, the two compartments are surrounded with a semipermeable wall, or they are surrounded by a laminated wall. Optionally, system 10 can be manufactured by first fabricating one compartment by pressing in a standard tableting machine a drug to form a predetermined shaped compartment, and while the first shaped-pressed compartment is in the tablet pressing machine, a layer of a partition forming hydrogel is added thereto, and then the other compartment is formed by pressing drug to first compartment. Finally, the two adjacent compartments are surrounded with a wall formed of a semipermeable material, and a passageway is drilled through the wall into each compartment to form system 10 with two distinct compartments and two distinct orifices for dispensing two drugs from system 10. The compartment also can be joined by other methods including heat sealing, pressing, consecutively casting the compartments in a dual cavity mold, overlaying, and the like.

The walls, lamina and partition forming the system can be joined by various techniques such as high frequency electronic sealing that provides clean edges and firmly formed walls, lamina and partitions. A presently preferred technique that can be used for forming the wall is the air suspension procedure. This procedure consists in suspending and tumbling the drug or osmagent dual compartment forming device in a current of air and a wall forming, or lamina forming, composition until the wall or lamina is applied to the drug. The air suspension procedure is well-suited for independently forming the walls and lamina. The air suspension procedure is described in U.S. Pat. No. 2,799,241; in *J. Am. Pharm. Assoc.*, Vol. 48, pages 451 to 459, 1959; and ibid., Vol. 49, pages 82 to 84, 1960. Other wall and laminating techniques such as pan coating can be used in which the materials are deposited by successive spraying of the polymer solution on the drug accompanied by tumbling in a rotating pan. Other standard manufacturing procedures are described in *Modern Plastics Encyclopedia*, Vol. 64, pages 62 to 70, 1969; and in *Pharmaceutical Sciences*, by Remington, 14th Ed., pages 1926 to 1678, 1970, published by Mack Publishing Co., Easton, Pa.

The microporous lamina, in optional manufacturing embodiments, can be manufactured with microporous wall forming polymers that are commercially available, or they can be made by art known methods. The microporous materials can be made and then manufactured into a device by etched nuclear tracking, by cooling a solution of flowable polymer below its freezing poing whereby solvent evaporates from the solution in the form of crystals dispersed in the polymer, and then curing the polymer followed by removing the solvent crystals, by cold or hot stretching of a polymer at low or high temperatures until pores are formed, by leaching from a polymer soluble pore forming component by use of an appropriate solvent, and by dissolving or leaching a pore former from the wall of a device in operation in the environment of use. Processes for preparing microporous materials are described in *Synthetic Polymer Membranes*, by R. E. Kesting, Chapters 4 and 5, 1971 published by McGraw Hill, Inc; *Chemical Reviews, Ultrafiltration*, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat. Nos. 3,565,259; 3,615,024; 3,751,536; 3,801,692; 3,852,224; and 3,849,528.

Generally, the semipermeable wall will have a thickness of 2 to 20 mils, with a presently preferred thickness of 4 to 12 mils. The partition between the compartment generally will have a thickness of 1 mil to 7 mils, with a presently preferred thickness of 2 to 5 mils. In laminated walls, the lamina will have a thickness of 2 to 10 mils with a presently preferred thickness of 2 to 5 mils. Of course, thinner and thicker walls, lamina and partitions for use with numerous drugs and osmagenta are within the scope of the invention.

Exemplary solvents suitable for manufacturing the wall and the lamina include inert inorganic and organic solvents that do not adversely harm the wall and lamina materials, and the final system. The solvents broadly include members selected from the group consisting of aqueous solvents, alcohols, ketones, esters, ethers, aliphatic hydrocarbons, halogenated solvents, cycloaliphatic aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol, and mixtures thereof.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

As osmotic delivery device for the controlled and continuous delivery of the two beneficial drugs hydralazine hydrochloride and metoprolol fumarate to a biological environment of use is made as follows: first, a reservoir forming composition for housing in one compartment is compounded from 50 mg of hydralazine hydrochloride, 208.5 mg of mannitol, 8 mg of hydroxypropyl methylcellulose and 8 mg of stearic acid by mixing the hydralazine hydrochloride and the mannitol and then passing the mixture through a 40-mesh screen, next, the hydroxypropyl methylcellulose is dissolved in a 70/30 (w/w%) ethanol-water solution and the hydralazine-mannitol mixture added to the wet hydroxypropyl methylcellulose and all the ingredients blended for 10 minutes. Next, the blend is passed through a 10-mesh screen and spread on a tray and dried in a forced air oven at 50° C. for 18–24 hours. The dried blend is passed through a 20-mesh screen, placed in a mixer, and the stearic added to the blend and the mixing continued for 10 minutes.

A second reservoir forming composition comprising 190 mg of metoprolol fumarate, 8.4 mg of sodium bicarbonate, 10.6 mg of polyvinyl pyrrolidone and 3.2 mg of magnesium stearate is made by first mixing the metoprolol fumarate with sodium bicarbonate and passing the mixture through a 40-mesh screen, then, the polyvinyl pyrrolidone is mixed with 15 ml of an ethanol and 5 ml of water solution, and the freshly prepared polyvinyl pyrrolidone solution is added slowly with mixing to the metoprolol fumarate-sodium bicarbonate mixture. The ingredients are mixed for 20 minutes, passed through a 10-mesh screen and dried in a forced air oven for 24 hours. Next, the dried blend is passed through a 20-mesh screen, placed in a mixer, the magnesium stearate added and the ingredients again blended to yeild the reservoir composition.

Figure 7:
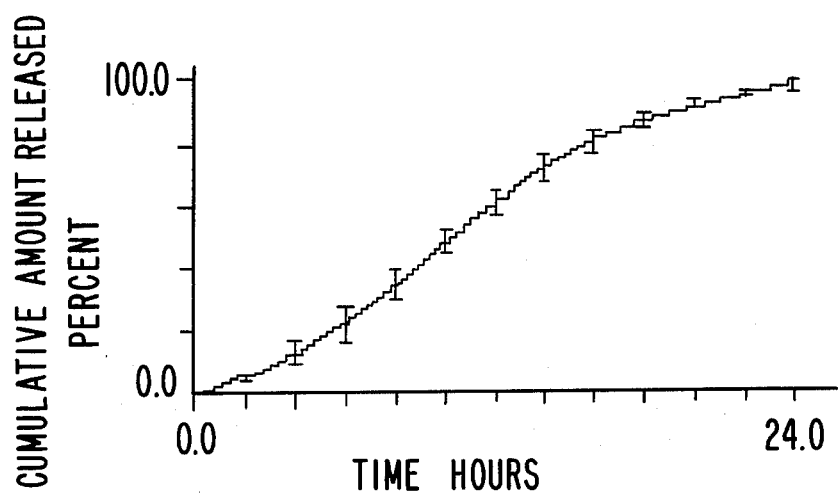
FIG. 7 is a graph illustrating the cumulative amount of drug released from one compartment of a device; and, FIG. 8 is a graph illustrating the cumulative amount of drug released from the other compartment of the device.
Figure 8:
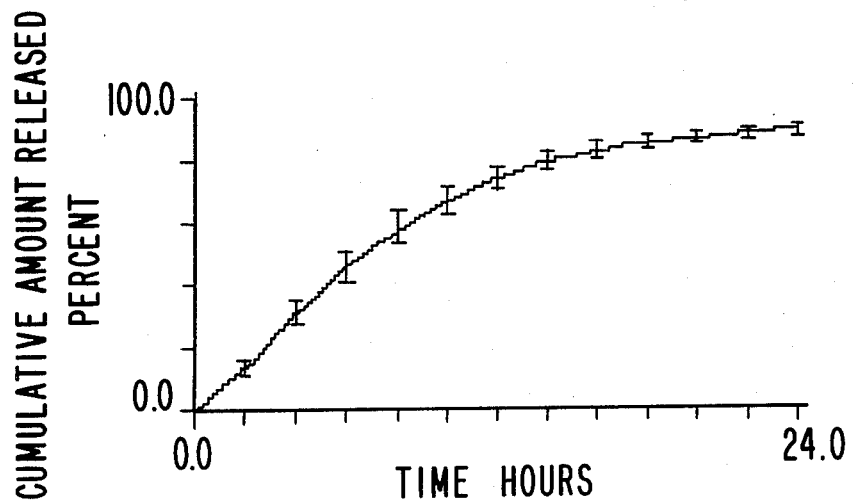

Next, 275 mg of the hydralazine drug formulation reservoir, as described above, is placed into a 7/16 inch biconvex oval tablet die, and the turret of the tablet compression machine turned until the load reaches the compression point with the drug formulation compressed into the shape of the die. The turret is reversed back to the loading position and 100 mg of polyethylene oxide is spread over the compressed drug formulation to form a partition. Next, the turret is turned to the compression point to assist in forming the hydrogel partition. Then, the turret is returned to the loading position, and 200 mg of the metoprolol fumarate drug formulation is added to the die in contact with the partition, and the formulation pressed against the partition. The two united compartments then were coated in an air suspension machine with a wall of semipermeable cellulose acetate with a wall forming composition comprising 40% cellulose acetate having an acetyl content of 32%, 42% cellulose acetate having an acetyl content of 39.8% and 18% hydroxypropyl methylcellulose, dissolved in an 80 to 20 parts by weight of a methylene chloride-methanol solvent. The two compartments are coated with the cellulose acetate to form a semipermeable wall having a thickness of 7 mils. The coated compartments are dried in a forced air oven at 50° C. for one week. Then, an orifice is laser drilled through the wall into one compartment, and then an orifice is laser drilled through the wall communicating with the other compartment. The orifices have a diameter of 9 mils for delivering each drug from the device. The osmotic systems had an average release rate of 2 mg/hr for hydralazine hydrochloride, and a release rate average of 13 mg/hr for metoprolol fumarate. Accompanying FIG. 7 depicts the cumulative amount released over a delivery period of 24 hours for hydralazine hydrochloride, and FIG. 8 depicts the cumulative amount of metoprolol fumarate released from the device over 24 hours. The bars on the graphs indicate the minimum and maximum values, or the total range of experimental data.

EXAMPLE 2

The procedure of Example 1 is repeated and a device is provided housing in the first compartment a drug formulation comprising 50 mg of hydralazine hydrochloride, 208.5 mg of mannitol, 8.0 mg of hydroxypropyl methylcellulose and 8.2 mg of stearic acid, and the drug formulation in the second compartment comprises 190 mg of metoprolol fumarate, 10.2 mg of polyvinyl pyrrolidone and 3.0 mg of magnesium stearate.

EXAMPLE 3

The procedure of Example 1 is followed in this example. The osmotic, oral device provided by this example contains in the first compartment a drug formulation comprising 50 mg of hydralazine hydrochloride, 208.5 mg of mannitol, 8.0 mg of hydroxypropyl methylcellulose and 8.2 mg of stearic acid, and in the second compartment a drug formulation consisting essentially of 290 mg of oxprenolol sebacinate, 96.1 mg of sodium bicarbonate, 16.3 mg of polyvinyl pyrrolidone and 4.0 mg of magnesium stearate. The oxprenolol sebacinate drug reservoir formulation is prepared by first mixing the oxprenolol sebacinate and sodium bicarbonate and passing the mixture through a 20-mesh sieve, mixing the polyvinyl pyrrolidone with ethanol-water solution and then adding the wet polyvinyl pyrrolidone to the oxprenolol sebacinate sodium bicarbonate blend. Then, the just prepared wet granulation is passed through a number 10-sieve, and dried overnight in a forced air oven at 50° C. Next, the dried granules are passed through a number 20-sieve and the magnesium stearate added thereto. The coating and tableting procedures are as set forth in Example 1. The device released hydralazine hydrochloride at the rate of 3 mg/hr and oxprenolol sebacinate at the rate of 8 mg/hr.

EXAMPLE 4

The procedure of Example 1 is followed in this example to produce an osmotic device comprising a first compartment containing a hydralazine hydrochloride drug formulation, a second compartment containing a metropolol fumarate drug formulation and a partition consisting essentially of polyacrylamide hydrogel, sold under the trademark Cyanamer ®A 370, a hydrogel polymer of approximately 200,000 mol. wt.

EXAMPLE 5

The procedures of Examples 1 and 2 are followed for producing delivery devices housing separately in the compartments salbutamol and theophylline, chlordiazepoxide hydrochloride and clidinium bromide, acetaminophen and oxycodone, pindolol and thiazide, cimetidine and salbutamol, burimamide and pirenzepine, cimetidine and propantheline, cimetidine and isopropamide, and the like.

EXAMPLE 6

The procedure of Example 1 is repeated in this example with all conditions as previously described with the drug in the first compartment a member selected from the group consisting of a hypnotic, sedative, psychic energizer, tranquilizer, anticonvulsant, muscle relaxant, antiparkinson drug, analgesic, anti-inflammatory, anesthetic, muscle contractant, anti-microbial, antimalarial, hormone, sympathomimetic and diuretic, and the drug in the second compartment is a different drug selected from the same group.

EXAMPLE 7

The procedure of Example 1 is repeated in this example with all the conditions as described except that the device is designed as an ocular osmotic insert and the ophthalmic drug in the first compartment is pilocarpine hydrochloride and the drug in the second compartment is epinephrine hydrochloride.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the systems illustrated and described can be made without departing from the spirit of the invention.

We claim:

1. An osmotic therapeutic device for the controlled delivery of beneficial drugs to a biological environment, the device consisting essentially of:
   (a) a wall formed of a semipermeable material permeable to the passage of an external fluid present in the environment and substantially impermeable to the passage of drug, the semipermeable wall surrounding and forming;
   (b) a first compartment containing a drug formulation that exhibits an osmotic pressure gradient across the semipermeable wall against an external fluid;
   (c) a second compartment containing a drug formulation that exhibits an osmotic pressure gradient across the semipermeable wall against an external fluid;
   (d) a partition positioned between the first and second compartments, which partition is formed of a hydrogel that expands in the presence of fluid;
   (e) a first orifice in the wall communicating with the first compartment and the exterior of the device for delivering drug formulation from the first compartment to the environment over a prolonged period of time; and,
   (f) a second orifice in the wall communicating with the second compartment and the exterior of the device for delivering drug formulation from the second compartment to the environment over a prolonged period of time.

2. The osmotic therapeutic device for the controlled delivery of beneficial drugs according to claim 1, wherein when the device is in operation in the environment of use, fluid from the environment is imbibed through the wall into (1) the first compartment in a tendency towards osmotic equilibrium at a rate determined by the permeability of the wall and the osmotic pressure gradient across the wall, thereby forming a solution containing drug that is delivered through the first orifice from the device at a controlled rate over a prolonged period of time, and into (2) the second compartment in a tendency towards osmotic equilibrium at a rate determined by the permeability of the wall and the osmotic pressure gradient across the wall, thereby forming a solution containing drug that is delivered through the second orifice from the device at a controlled rate over a prolonged period of time.

3. The osmotic therapeutic device for the controlled delivery of beneficial drugs according to claim 1, wherein the drug formulation in the first compartment comprises a dosage unit amount of drug and an osmagent.

4. The osmotic therapeutic device for the controlled delivery of beneficial drugs according to claim 1, wherein the drug formulation in the second compartment comprises a dosage unit amount of drug and an osmagent.

5. The osmotic therapeutic device for the controlled delivery of beneficial drugs according to claim 1, wherein the first and second compartments contain different drugs.

6. The osmotic therapeutic device for the controlled delivery of beneficial drugs according to claim 1, wherein the device is adapted for oral administration for delivering drugs to the gastrointestinal tract.

7. The osmotic device for the controlled delivery of the beneficial drug according to claim 1 wherein the wall is formed of a member selected from the group consisting of cellulose acylate, cellulose diacylate, cellulose triacylate, cellulose acetate, cellulose diacetate and cellulose triacetate, ethylcellulose and cellulose acetate butyrate.

8. The osmotic device for the controlled delivery of a beneficial drug according to claim 1 wherein the hydrogel is cross-linked.

9. The osmotic device for the controlled delivery of beneficial drug according to claim 1, wherein the hydrogel can expand from a rested to an expanded state in the presence of exterior fluid imbibed into the osmotic device, whereby through the combined operations of the external fluid being imbibed through the wall into the first compartment and the second compartment, and the expanding hydrogel, solution containing drug is delivered through the first orifice and the second orifice from the first compartment and the second compartment to the exterior of the device over time.

10. An osmotic therapeutic device for the controlled delivery of beneficial drugs to a biological environment, the device consisting essentially of:
(a) a laminated wall formed of a semipermeable lamina in laminar arrangement with a microporous lamina, the laminated wall surrounding and forming;
(b) a first compartment containing a drug formulation that exhibits an osmotic pressure gradient across the laminated wall against an external fluid;
(c) a second compartment containing a drug formulation that exhibits an osmotic pressure gradient across the laminated wall against an external fluid;
(d) a partition positioned between the first compartment and the second compartment, which partition is formed of a hydrogel that expands in the presence of fluid;
(e) a first orifice in the laminated wall communicating with the first compartment and the exterior of the device for delivering drug formulation from the first compartment to the environment over a prolonged period of time;
and,
(f) a second orifice in the laminated wall communicating with the second compartment and the exterior of the device for delivering drug formulation from the second compartment to the environment over a prolonged period of time.

11. The osmotic therapeutic device for the controlled delivery of beneficial drugs according to claim 10 wherein when the device is in operation in the environment of use, fluid from the environment is imbibed through the laminated wall into (1) the first compartment in a tendency towards osmotic equilibrium at a rate determined by the permeability of the wall and the osmotic pressure gradient across the wall, thereby forming a solution containing drug that is delivered through the first orifice from the device at a controlled rate over a prolonged period of time, and into (2) the second compartment in a tendency towards osmotic equilibrium at a rate determined by the permeability of the wall and the osmotic pressure gradient across the wall, thereby forming a solution containing drug that is delivered through the second orifice from the device at a controlled rate over a prolonged period of time.

12. The osmotic device for the controlled delivery of the beneficial drug according to claim 10, wherein the hydrogel expands from a rested to an expanded state in the presence of exterior fluid imbibed into the device, whereby through the combined operations of the exterior fluid being imbibed through the wall into the first compartment to form a solution containing drug, and into the second compartment to form a solution containing drug, drug is delivered through the first orifice and through the second orifice from the first compartment and the second compartment to the exterior of the device over a prolonged period of time.

13. The osmotic therapeutic device for the controlled delivery of beneficial drugs according to claim 10 wherein the drug formulation in the first compartment comprises a dosage unit amount of drug and an osmagent.

14. The osmotic therapeutic device for the controlled delivery of beneficial drugs according to claim 10 wherein the drug formulation in the second compartment comprises a dosage unit amount of drug and an osmagent.

15. The osmotic therapeutic device for the controlled delivery of beneficial drugs according to claim 10 wherein the first and second compartments contain different drugs.

16. The osmotic therapeutic device for the controlled delivery of beneficial drugs according to claim 10 wherein the device is adapted for oral administration for delivering drugs to the gastrointestional tract.

17. The osmotic therapeutic device for the controlled delivery of beneficial drugs according to claim 10 wherein the semipermeable lamina faces the compartments and the microporous lamina faces the environment.

18. The osmotic therapeutic device for the controlled delivery of beneficial drugs according to claim 10 wherein the microporous lamina faces the compartments and the semipermeable lamina faces the environment.

* * * * *